United States Patent [19]

Chiesi et al.

[11] Patent Number: 4,824,841
[45] Date of Patent: Apr. 25, 1989

[54] AQUEOUS PHARMACEUTICAL FORMULATIONS OF PIROXICAM MONOHYDRATE

[75] Inventors: Paolo Chiesi; Luciana Pavesi, both of Parma, Italy

[73] Assignee: Chiesi Farmaceutici S.P.A., Parma, Italy

[21] Appl. No.: 941,819

[22] Filed: Dec. 15, 1986

Related U.S. Application Data

[63] Continuation of Ser. No. 788,783, Oct. 18, 1985, abandoned.

[30] Foreign Application Priority Data

Oct. 22, 1984 [IT] Italy ............................... 23263 A/84

[51] Int. Cl.$^4$ ............................................. A61K 31/54
[52] U.S. Cl. .................................................. 514/226.5
[58] Field of Search ...................... 514/222; 544/48, 49

[56] References Cited

U.S. PATENT DOCUMENTS

| | | | |
|---|---|---|---|
| 3,853,862 | 12/1974 | Lombardino | 544/49 |
| 4,116,964 | 9/1978 | Zinnes et al. | 544/49 |
| 4,309,427 | 1/1982 | Lombardino | 544/49 |
| 4,434,163 | 2/1984 | Lombardino | 514/222 |
| 4,434,164 | 2/1984 | Lombardino | 514/222 |
| 4,628,053 | 12/1986 | Fries | 514/222 |
| 4,636,498 | 1/1987 | LaMattina | 514/222 |

FOREIGN PATENT DOCUMENTS 101178 2/1984 European Pat. Off. .

OTHER PUBLICATIONS

Chem. Abst. 99: 187283(d) (1983)—Van Haeringen et al.
Chem. Abst. 101: 46537(n)91984)—Bordner et al.
Chem. Abst. 101: 198023e (1984)—Bregni et al.
Textbook of Organic Chem.—Noller—1966—pp. 198–199.
Advanced Organic Chemistry—2nd ed.—Mar. pp. 804–807 (1977).
3rd Inter—Congress of Pharm. Tech.—Paris, France—1983 "Etude Des Parametres Influencant Atvitesse De Dissolution Du Piroxicame."
Lombardino et al., Journal of Medicinal Chemistry (1972), vol. 15, No. 8, pp. 848–849.
Pharmacological & Biochemical Properties of Drug Substances, vol. 3, published by American Pharm. Ass., Academy of Pharm. Sciences (1985), p. 324.

Primary Examiner—Douglas W. Robinson
Attorney, Agent, or Firm—Bucknam and Archer

[57] ABSTRACT

The present invention relates to a process for the transformation of Piroxicam, N-(2-pyridyl)-2-methyl-4-hydroxy-2H-1, 2-benzothiazine-3-carboxamide 1,1-dioxide into an hydrated form, suitable for oral, topic or parenteral administration.

6 Claims, No Drawings

AQUEOUS PHARMACEUTICAL FORMULATIONS OF PIROXICAM MONOHYDRATE

This application is a continuation of U.S. Ser. No. 788,783 filed Oct. 18, 1985 now abandoned.

More specifically, the invention relates to the use of Piroxicam in the monohydrated form in aqueous compositions for oral, topical or parenteral administration.

SUMMARY OF THE INVENTION

Piroxicam monohydrate is represented by the following formula:

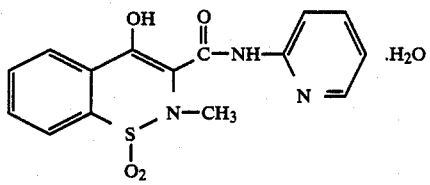

The crystallographic characteristics of Piroxicam monohydrate are described in J. Border - Acta Cryst. C 40, 989, 1984.

Piroxicam is a compound effectively used in the treatment of artrorrehumatic affections, due to its remarkable analgesic and antiphlogistic activity.

Aqueous formulations containing Piroxicam, in form of a salt with both inorganic and organic bases, such as alkylamines and alkanolamines (EP No. 66459), amino acids (EP No. 66458) and combinations of polyhydroxylated alcohol with alkanolamines (EP No. 101178) are known; on the contrary, aqueous formulations containing Piroxicam in the free form are now known.

It is difficult to obtain aqueous compositions of Piroxicam, due to its particular chemico-physical characteristics. In fact, besides being insoluble in wate when formulated in non-aqueous vehicles, such as excipients for creams, ointments, etc., containing even traces of water, it undergoes to the transformation into its hydrated form, which crystallizes in the medium, thus producing large yellow agglomerates.

It has now surprisingly been found, and it is an object of the present invention, that Piroxicam in the monohydrated form, prepared according to one of the methods hereinbelow described, does not form agglomerates, with a constant size of the particles suspended or dispersed in the aqueous compositions. Said characteristics advantageously allows to use the compound per se in pharmaceutical compositions for oral, topical or parenteral administration, not requiring the further use of organic or inorganic bases as salifying agents for the active ingredient. A further important advantage of the compositions according to the invention is provided by their remarkable stability for a long period of time.

The process for preparing Piroxicam monohydrate is very simple and unexpensive.

Generally Piroxicam, obtained as described in U.S. Pat. No. 3,591,584 by J. G. Lombardino, is dissolved in an aqueous solution, by addition of an inorganic base of an alkali or alkali earth metal, preferably potassium hydroxide, or an organic base, generally water soluble alkyl- or alkanol-amines, such as ethanolamine or aqueous ammonia.

At least one molar equivalent of an inorganic acid, such as hydrochloric acid, sulfuric acid, etc., or a water soluble organic acid, such as acetic or propionic acid, is added to the resulting solution.

The reaction is carried out at temperatures ranging from 20° to 100° C., for 30 minutes to 3 hours.

After completion of the reaction, the yellow precipitate of Piroxicam monohydrate is easily recovered by means of conventional techniques, such as filtration, washing with water, drying in oven at temperatures between 20° and 60° C., until constant weight.

The obtained solid may be used as it is, or mycronized into particles of 2–10 $\mu$ size.

The following examples further illustrate the present invention, without limiting the scope thereof.

EXAMPLE 1

To a 500 ml flask containing 30 ml of water, 18 ml (0.032 mole) of 10% KOH and 10.3 g (0.031 mole) of Piroxicam were added.

The resulting yellow solution was added, under stirring, with 11 ml (0.033 mole) of 3N HCl, thereafter with water to a final volume of about 300 ml.

The reaction mixture was stirred at 30°–35° C. for about 2 hours, the obtained yellow precipitate was filtered, thoroughly washed with water, and dried in oven, under water pump vacuum, at 40° C. for about 30 minutes, then at 60° C. till constant weight.

10.8 Grams (100% yield) of Piroxicam monohydrate ($C_{15}H_{25}N_3O_5S \cdot H_2O$) were obtained; m.p. 197°–200° C.

| Analysis | |
|---|---|
| Potentiometric titre as the monohydrate | 98.24% |
| Water K.F. | 5.43% |
| Differential Scannig Calorimetry (D.S.C.). | |

A peak corresponding to the hydration water at about 125°–130° C. and the peak characteristic of Piroxicam at 200° C. appear.

| | |
|---|---|
| Starting temperature | 50° C. |
| Temperature gradient | 10° C./min. |
| Final temperature | 250° C. |

The product was characterized also by spectrophotometric IR and NMR techniques, as well as elemental analysis.

EXAMPLE 2

To 600 ml of water, 25 ml of 30% ammonia was added, thereafter 10 g of Piroxicam was dissolved.

To the clear yellow solution, 20 ml of glacial acetic acid were added dropwise, under stirring, to adjust the pH to 5–5.5.

Stirring was continued for about 30 minutes, then the reaction mixture was filtered.

The obtained residue was thoroughly washed with water and dried in oven at 45°–50° C., to give a markedly yellow powder.

The chemico-physical characteristic of the compound were the same as those of Example 1.

Prioxicam monohydrate, obtained according to the above described processes, showed an antiinflammatory activity, by oral route in the rat, analogous to that of anhydrous Piroxicam, in the standard test of carrageening oedema, according to the procedure of C.A. Winter et al. Proc. Soc. Exp. Biol. Med. 111, 544, 967.

Piroxicam monohydrate may thus be used, similarly to anhydrous Piroxicam, in the treatment of arthroreuhmatic affections.

The present invention further relates to the preparation of pharmaceutical compositions containing Piroxicam monohydrate as the active ingredient, in weight ratios of 0.2 to 5%, together with pharmaceutically acceptable excipients.

Said compositions may be administered by oral or parenteral route, in form of suspensions, or by topical route, in form of creams, ointments or gels.

For the preparation of pharmaceutical composition for oral administration in unitary dosage form, the active ingredient may be dispersed in water, by means of conventional vehicles and excipients, such as hydrophilic colloids deriving from cellulose, such as carboxymethylcellulose or mycrocrystalline cellulose; colloidal silicates, such as Al and Mg colloidal hydrate silicate; carbohydrates, such as saccharose; wetting agents, such as glycerol, sorbitol, polysorbate. The suspension may be stabilized by means of citrate or phosphate buffer, at pH ranging from 4.5 to 6.

In the formulations for parenteral administration, the active ingredient is mycronized in particles of 2–10 $\mu$ size, preferably 2–5 $\mu$, and formulated in aqueous suspensions containing appropriate vehicles and excipients, such as Al and Mg silicate; hydrophylic colloids, such as carboxymethylcellulose, methylcellulose; flocculation agents, such as aluminium chloride or monosodium citrate; and wetting agents, such as polysorbate. The suspension may be stabilized at pH about 4.5–6, using suitable buffers, keeping isotonicity conditions by addition of sodium chloride.

The formulation is prepared in aseptic conditions, using apyrogenic and sterile starting materials.

In the formulations for topical adminstration, the active principle may be disperded in a cream containing 20–60% water, preferably 50%, and a fatty phase containing oils and waxes of natural or synthetic course; emulsifying agents such as glycerol esters or sorbitol with fat acids or polyoxyethylenate fat alcohols. To the aqueous phase, polyols such as glycerol, sorbitol or propylene glycol may be added.

The compositions according to the present invention so prepared have been verified chemically and physically stable, even for a long time after the preparation.

Exemplificative formulations are reported hereinbelow.

| Suspension formulation for oral administration | | |
|---|---|---|
| Piroxicam monohydrated | g | 0.210 |
| (corresponding to 0.200 g of Piroxicam) | | |
| Polysorbates | g | 0.100 |
| Saccharose | g | 24.000 |
| Glycerol | g | 4.000 |
| Mycrocrystalline cellulose | g | 1.246 |
| Carboxymethylcellulose | g | 0.154 |
| Methyl p-hydroxybenzoate | g | 0.100 |
| Propyl p-hydroxybenzoate | g | 0.010 |

| -continued | | | |
|---|---|---|---|
| Ethyl alcohol | | g | 0.700 |
| Purified water and phosphate buffer at pH 4.5–5 | q.s. to | ml | 100. |

| Suspension formulation for parenteral administration | | |
|---|---|---|
| Mycronyzed Piroxicam monohydrate | mg | 21.0 |
| Al e Mg hydrated colloidal silicate | mg | 8.0 |
| Carboxymethylcellulose | mg | 24.0 |
| Monobasic sodium citrate | mg | 5.0 |
| Sodium chloride | mg | 14.3 |
| Polysorbates | mg | 2 |
| Water | q.s to ml | 2.0. |

The pH of the formulation is stabilized to values ranging from 4.5 to 6 by means of citrate or phosphate buffer.

| Cream formulation | | |
|---|---|---|
| Piroxicam monohydrate | g | 1.050 |
| Polyoxyethylen fatty alcohol | g | 2.000 |
| Propylen glycol | g | 7.000 |
| Cetostearilic alcohol | g | 3.500 |
| Fatty acids polyethylenglycolic ester | g | 18.000 |
| Water, preservatives and buffering agents to pH 4.5–6 | q.s. to g | 100.00. |

We claim:

1. A pharmaceutical composition for the treatment of inflammatory diseases, comprising as the active agent 0.2–5% by weight of N-(2-pyridyl)-2-methyl-4-hydroxy-2H-1, 2-benzothiazine-3-carboxamide 1, 1-dioxide monohydrate, in the form of a yellow crystalline powder dispersed in an oil/water emulsion or suspended in water, said composition being stabilized with respect to crystal growth, crystal conversion and agglomerate formation in aqueous medium by maintaining a pH from about 4.5 to about 6, said composition further comprising conventional excipients.

2. A pharmaceutical composition according to claim 1 which is a suspension for oral or parenteral administration, wherein said active agent is suspended in water.

3. A pharmaceutical composition according to claim 1 which is a cream, an ointment, a lotion, or a gel for topical administration, wherein said active agent is dispersed in an oil/water emulsion.

4. A pharmaceutical composition according to claim 1 wherein said active ingredient is stabilized with a citrate or phosphate buffer at pH 4.5–6.

5. The composition according to claim 1 wherein said monohydrate of N-(2-pyridyl)-2-methyl-4-hydroxy-2H-1, 2-benzothiazine-3-carboxamide 1,1-dioxide contains 5.43% water by weight.

6. A method of treatment of a subject affected by an inflammatory condition which consists of administering to said subject a therapeutically effective amount of N-(2-(pyridyl)-2-methyl-4-hydroxy-2H-1,2-benzothiazine-3-carboxamide 1,1-dioxide monohydrate in a pharmaceutical composition having pH about 4.5 to 6, stabilized with respect to crystal growth, crystal conversion and agglomerate formation in an aqueous medium.

* * * * *